United States Patent
Hood et al.

(10) Patent No.: US 6,548,597 B2
(45) Date of Patent: Apr. 15, 2003

(54) POLYMERIC COMPOSITION

(75) Inventors: David K. Hood, Basking Ridge, NJ (US); Stephen L. Kopolow, Plainsboro, NJ (US); Michael Tallon, Aberdeen, NJ (US); Yoon Tae Kwak, Woodcliff Lake, NJ (US); Laurence Senak, West Orange, NJ (US); Drupesh Patel, Jersey City, NJ (US); John Mc Kittrick, Jersey City, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/784,268

(22) Filed: Feb. 15, 2001

(65) Prior Publication Data

US 2002/0058750 A1 May 16, 2002

Related U.S. Application Data

(63) Continuation-in-part of application No. 09/663,010, filed on Sep. 15, 2000.

(51) Int. Cl.[7] .................................................. C08F 2/16

(52) U.S. Cl. ...................................................... 524/804
(58) Field of Search ......................................... 524/804

(56) References Cited

U.S. PATENT DOCUMENTS

| | | | | | |
|---|---|---|---|---|---|
| 4,361,452 A | * | 11/1982 | Clarke | ........................... | 156/71 |
| 5,409,771 A | * | 4/1995 | Dahmen | ...................... | 428/327 |
| 5,432,210 A | * | 7/1995 | Bogan | ......................... | 523/201 |
| 5,561,190 A | * | 10/1996 | Avison | ......................... | 524/522 |
| 5,667,885 A | * | 9/1997 | Nguyen | ...................... | 428/327 |
| 5,753,360 A | * | 5/1998 | Jones | ......................... | 428/323 |
| 6,180,255 B1 | * | 1/2001 | Valentini | ..................... | 428/500 |
| 6,197,863 B1 | * | 3/2001 | Eck | ............................ | 524/430 |

* cited by examiner

*Primary Examiner*—Edward J. Cain
(74) *Attorney, Agent, or Firm*—Walter Katz; William J. Davis; Marilyn J. Maue

(57) ABSTRACT

A stable, aqueous polymeric composition which forms a clear to translucent film upon application to a substrate includes, by weight, 5–75% of (a) a water-soluble polymer having (b) in situ-formed, substantially water-insoluble resinous particles of said polymer substantially uniformly dispersed therein, and (c) 25–95% of water.

39 Claims, 1 Drawing Sheet

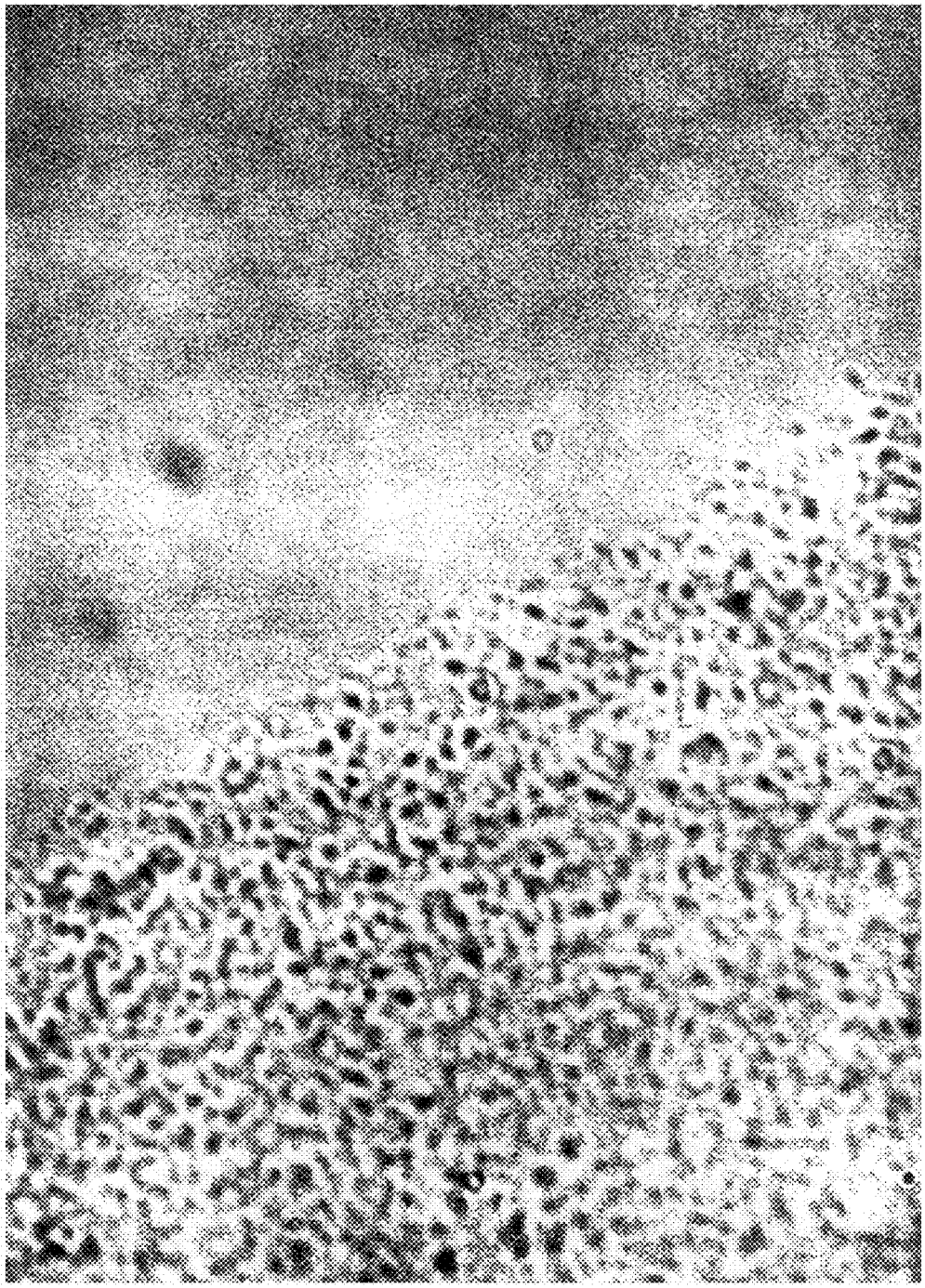

POLYMERIC COMPOSITION

CROSS-REFERENCE TO RELATED U.S. PATENT APPLICATIONS

This application is a continuation-in-part of co-pending U.S. patent application Ser. No. 09/663,010, filed Sep. 15, 2000.

BACKGROUND OF THE INVENTION

1. Field of the Invention

This invention relates to polymeric compositions, and, more particularly, to a non-continuous, vinyl lactam polymeric composition having two phases therein, particularly suitable for making clear to translucent, water-resistant, color inkjet receptive films on a substrate.

2. Description of the Prior Art

Polymeric compositions of vinyl lactam monomers generally are one-phase, soluble, high viscosity materials. These compositions are found in a variety of commercial applications such as film formers, dye transfer inhibitors, rheology modifiers, dispersants, excipients, and drug delivery. Aqueous gels of these monomers can also be prepared by light covalent or associative crosslinking of polymer chains resulting in a highly swellable, one phase material of high viscosity. These compositions are effective thickeners for use in personal care formulations such as hair care products.

Niessner, in U.S. Pat. Nos. 5,149,750 and 5,180,804, disclosed finely divided, water-swellable gel-like, water-swellable copolymers by polymerization of comonomers in the presence of a surfactant.

Liu, in U.S. Pat. No. 5,997,855, described a homogeneous terpolymer for hair care use, however, without a crosslinking agent.

Kopolow, in U.S. Pat. No. 5,130,121, described personal care compositions containing a stabilized cosmetically-active product obtained by in situ polymerization of a water-soluble vinyl monomer in the presence of discrete microdroplets of a cosmetically-active oil in water.

Blankenburg, in U.S. Pat. No. 5,635,169 and 6,107,397, also described uncrosslinked aqueous copolymer dispersions of nonionic water-soluble monomers with N-vinyl groups, and hydrophobic monomers.

Steckler, in U.S. Pat. No. 3,878,175, disclosed highly absorbent spongy gel polymer materials by simultaneously copolymerizing and partially crosslinking a comonomer mixture of an alkyl acrylate and a heterocyclic N-vinyl monomer containing a carbonyl functionality in the presence of a hydrophobic liquid diluent in which the final polymer is insoluble.

Markus, in U.S. Pat. No. 2,810,716, described a process for making swellable resins by copolymerizing monomers in the presence of a water-soluble non-redox divalent-ion containing salt.

Tseng, in U.S. Pat. Nos. 5,393,854 and 5,717,045 disclosed a one-phase, aqueous gel of crosslinked copolymers of vinyl pyrrolidone and dimethylaminoethyl methacrylate for use in hair care products. The crosslinking agent was 1-vinyl-3-(E)-ethylidene pyrrolidone. The gels had a Brookfield viscosity of between 60,000 and 100,000.

These references illustrate the desire of the art to produce a continuous network of polymer molecules, or microgel which is a one-phase system, and of high viscosity.

Another application for polymeric compositions is in color ink-jet printing. The advent of color inkjet printing has been instrumental in fueling the print-on-demand revolution and has also created a number of challenges. Often, the surface of the desired media does not possess the necessary properties for accepting the ink-jet ink. This results in long dry times and/or a poor ink-jet image. It has long been recognized that a surface treatment or media coating plays a critical role in the final print quality. Numerous media coatings are known in the art. They may contain any number of components and often consist of more than one layer. These ink-receptive coatings generally contain at least one hydrophilic polymer; often poly(vinylpyrrolidone) (PVP). In contrast to the teaching of the thickener art for personal care products, networked, highly swellable polymeric systems are undesirable in this application. Soluble PVP brings many benefits to properly formulated media coatings including rapid ink dry time, excellent print quality, highly resolved circular dots, and high, uniform optical density. Furthermore, copolymers of vinylpyrrolidone (VP) along with other suitable comonomers, such as dimethylaminoethyl methacrylate, acrylic acid, or vinyl acetate, have been used separately or in conjunction with PVP, to further optimize performance. Unfortunately, their resistance to water penetration can be weak. It is desired to provide long-term, excellent water-resistant qualities for such films.

Accordingly, it is an object of the present invention to provide an aqueous polymeric composition which is not a gel but a combination of film forming polymer and substantially, uniformly dispersed minute resinous particles that under suitable light magnification, shows the presence of two discrete phases therein, one which is a water soluble polymer and the other are in situ-formed, water-insoluble resinous particles.

Accordingly, another object of the invention is to provide an advantageously water-resistant color inkjet-receptive film coated with the defined polymer composition of the invention, which is capable of being printed from a color ink-jet printer to form superior water-resistant color images thereon.

Accordingly, another object of the invention is to provide a water-resistant film with improved light fastness, UV protection, and bleed reduction.

Accordingly, another object of the invention is to demonstrate the utility of these compositions for a variety of applications, including, but not limited to, dye transfer inhibitors, rheology modifiers, refractive index modifiers, UV protectants, fragrance and silicone delivery, dispersants, excipients, drug delivery, and in personal care formulations.

Another object herein is to provide a suitable process for making such a polymeric composition.

A feature of the invention is the provision of an aqueous polymeric composition suitable for forming clear to translucent, water-resistant coatings on a substrate.

IN THE DRAWINGS

The FIGURE is a photomicrograph of the aqueous polymeric composition of the invention showing the presence of two discrete phases therein.

SUMMARY OF THE INVENTION

What is described herein is a stable, aqueous polymeric composition which forms a clear to translucent film upon application to a substrate comprising, by weight, 5–75% of (a) a water-soluble polymer having (b) in situ-formed, substantially water-insoluble resinous particles of said polymer substantially uniformly dispersed therein, and (c) 25–95% of water.

Preferably the polymer is polyvinylpyrrolidone (PVP), poly(vinylcaprolactam) (PVCL), a copolymer of PVP and/or PVCL, and, optionally, one or more comonomers, including comonomers such as dimethylaminopropyl(meth) acrylamide (DMAPMA) and dimethylaminoethyl(meth) acrylate (DMAEMA). Preferably the polymer is a vinyl lactam polymer, optionally copolymerized with a methacrylate/acrylate and/or methacrylamide/acrylamide comonomer.

In this invention the composition includes particles having a size of <500μ, preferably <100μ, and optimally between >1 nm and <500μ.

Suitably the composition includes a substantially water-insoluble polymer which is a crosslinked or branched polymer, neutralized and/or quaternized, and/or functionalized quaternized. The ratio of (a):(b) is 20–95% to 5–80%, preferably 20–75% to 25–80%, and the crosslinking agent is a substantially water-insoluble compound, preferably pentaerythritol triallyl ether (PETE), or pentaerythritol tetraacrylate (PETA), preferably at least partially soluble in water, and the crosslinking agent is present in an amount of 0.02–0.5% by weight of said composition, most preferably 0.05–0.3%.

In this invention, the composition has a Brookfield viscosity of 1,000 to 45,000 cps, preferably 2,000 to 20,000.

As a feature of the invention there is provided herein a process for making a stable, aqueous polymeric composition which includes the steps of providing a reaction mixture of a water-soluble vinyl monomer, optionally with one or more water-soluble comonomers, a predetermined amount of a crosslinking agent and water, heating the mixture, then periodically adding a predetermined amount of an initiator, and polymerizing at about 30–130° C., optionally further including the step of diluting with water during or after the polymerization.

Suitably the crosslinking agent is present in an amount of 0.02–0.5 wt. % based on monomers present, and preferably is PETE or PETA, and the initiator is an azo initiator.

Another feature of the invention is the provision of formulations containing the above-described composition, made by such process, and films of the composition on a substrate.

The compositions herein may be dried if desired to provide the polymeric composition as a solid, and, if desired, the water soluble polymer extracted with a solvent. The dried stable polymeric composition thereby includes, by weight, (a) 20% to 95% of a water-soluble polymer, and (b) 5% to 80% of in situ-formed, substantially water-insoluble resinous particles of said polymer substantially uniformly dispersed therein.

DETAILED DESCRIPTION OF THE INVENTION

In accordance with this invention, there is provided herein an aqueous polymeric composition having two phases therein, a water-soluble polymeric phase and a discrete, water-insoluble polymer particle phase which is generated in-situ during the polymerization of the monomers. In the preferred forms of the invention, the polymerization is carried out in aqueous solution of a vinyl lactam monomer, such as vinyl pyrrolidone or vinyl caprolactam. Optionally a comonomer may be present to form a copolymer. Suitable comonomers include methacrylate/acrylate monomers, such as dimethylaminoethyl(meth)acrylate (DMAEMA) and/or methacrylamide/acrylamide monomers, such as dimethylaminopropylacrylamide (DMAPMA).

This stable, aqueous polymeric composition forms a clear to translucent film upon application to a substrate and comprises, by weight, 5–75% of (a) a water-soluble polymer having (b) in situ-formed, substantially water-insoluble resinous particles of said polymer substantially uniformly dispersed therein, and (c) 25–95% of water.

The invention will now be illustrated in more detail by reference to the following examples.

EXAMPLE 1

Two-Phase Polymeric Composition of VP/DMAPMA

1. To a 2-l kettle fitted with a nitrogen inlet tube, thermocouple, agitator, and feed lines was added 87.15 g of vinyl pyrrolidone monomer, (VP), 697 g Dl water and 0.275 g (0.25% based upon monomer) of pentaerythritol triallyl ether (PETE) as crosslinker.
2. Purged with nitrogen subsurface for 30 minutes.
3. Heated to 70° C.
4. In a separate container weighed out 22.69 g of dimethylaminopropyl methacrylamide (DMAPMA).
5. With kettle temperature at 70° C., stop subsurface nitrogen purge and purged above surface. Precharged 1.1 g DMAPMA from container.
6. Started continuous addition of the remaining DMAPMA (21.86 g) over 210 minutes at a flow rate 0.11 ml/minute. Once the DMAPMA flow started, initiated with first shot of Vazo® 67 in isopropanol (IPA) (Time 0).
7. Initiator was added in 5 separate shots at 0, 30, 60, 150 and 210 minutes. 0.2 g of Vazo® 67 in 1.0 g IPA was added for each shot and two 0.5 g IPA washes were made.
8. Held the reaction temperature overnight at 70° C.
9. When residual VP level was below 400 ppm, diluted the batch with 266.7 g of Dl water.
10. Cooled batch to 50° C.
11. Neutralized the batch with conc. HCl to pH of 6.2–6.8 at 50° C. Room temperature pH was 6.8–7.2. Required approximately 14 g of conc. HCl.
12. Added 0.15 to 0.19% BTC 50 NF as preservative.
13. A two-phase, aqueous polymeric composition as shown in the Figure was obtained having the properties shown in Table 1 below.

EXAMPLE 2

The process of Example 1 was repeated using 5 separate shots of 0.3 g each of Vazo® 67 in 1.0 g of IPA. A similar polymeric composition as in Example 1 was obtained having the properties shown in Table 1.

EXAMPLE 3

The process of Example 1 was repeated using 5 separate shots of 0.4 g each of Vazo® 67 in 1 g of IPA, and 0.3 g of crosslinker. A similar polymeric composition was obtained, having the properties shown in Table 1.

Test Methods

Draw-downs from a 10% aqueous solution of the polymer composition of Examples 1–3 were cast onto a polyester substrate using a #38 Mayer bar and allowed to dry in an oven at 100° C. to give a dry coating thickness of approximately 9 microns.

Coated samples were then printed using a HP 832C printer at 600 DPI in "HP Premium Photo Paper" mode. Individual blocks of cyan(C), magenta(M), yellow(Y), and black(K), approximately 1"×1.75" in size, were printed side by side. Small blocks of C, M, Y, and K, approximately ⅛"×¼", are printed repeatedly down one edge of the page to provide a built-in time-line for measuring offset time as described below.

Off-set time is the minimum time required for no ink to transfer to a cover sheet placed on top of the print when contacted with a 4-lb roller immediately after printing. Ink transfer is determined at the point where the OD after testing dropped by a value of 0.2 units. Fast offset times are most desirable.

Water-resistance was measured by the following standard test procedure.

Water resistance was tested by placing the printed sheet at a 45° angle and dripping 10 ml of water at a constant rate (2 ml/min) over the surface for a maximum of 5 minutes. The samples were then judged by following rating system:

Poor—All ink removed in less than 1 minute.

Fair—Most or all ink removed between 1 and 5 minutes.

Moderate—Some (<50%) loss of ink after 5 minutes.

Good—Very slight (<10%) loss of ink with minimal running.

Very Good—100% water resistance with no change in appearance.

Results

The results of these tests, shown in Table 1, establish that the 2-phase polymeric composition of the invention exhibits an advantageous water-resistant property as well as desired viscosity and haze properties, and low offset times.

TABLE 1

| Ex. No. | X-Linker (%) | Initiator (g/shot) | Residual VP (ppm) | Haze (NTU) | Visco (cps) | Water-proof (min) | Offset Time* (Min) |
| --- | --- | --- | --- | --- | --- | --- | --- |
| 1 | 0.25 | 0.2 | 139 |  | 28,200 | 10 | <1 |
| 2 | 0.25 | 0.3 | 151 | 25.2 | 13,000 | 11 | <1 |
| 3 | 0.3 | 0.4 | 173 | 45.7 | 12,800 | 7 | <1 |

*The offset times of Examples 1–3 were < 1 minute.

EXAMPLE 4

Polymeric Composition of PVP

1. To a 2-l kettle fitted with a nitrogen inlet tube, thermocouple, agitator, and feed lines was added 131.81 g of VP, 756 g Dl water and 0.197 g PETE (0.15% based upon monomer).
2. Purged with nitrogen subsurface for 30 minutes.
3. Heated to 70° C.
4. Initiator was added at 0 and 30 minutes. 0.48 g of Vazo® 67 in 1.5 g IPA was added for each shot and two 1.0 g IPA washes were made.
5. Held the reaction temperature overnight at 70° C.
6. When residual VP was below 400 ppm, diluted the batch with 320.04 g Dl water.
7. Cooled batch to 50° C.
8. Added 0.15 to 0.19% BTC 50 NF as preservative.
9. The product was a 2-phase, polymerization composition with 40 to 70% resinous particles, whose soluble fraction had a molecular weight of 1,200,000 to 1,500,000.

EXAMPLE 5

Polymeric Composition of VP/DMAPMA/ Quaternized with Diethyl Sulfate

1. To a 2-l, kettle fitted with a nitrogen inlet tube, thermocouple, agitator, and feed lines was added 96.00 g of VP, 702.7 g Dl water and 0.36 g PETE (0.30% based upon monomer).
2. Purged with nitrogen subsurface for 30 minutes.
3. Heated to 70° C.
4. In a separate container weighed out 24.0 g DMAPMA and 74.7 g Dl water. Purged with nitrogen.
5. When kettle temperature was at 70° C., stopped subsurface nitrogen purge and purged above surface. Precharged 4.94 g DMAPMA/water from container.
6. Started continuous addition of the remaining DMAPMA/water (93.76 g) over 210 minutes. Flow rate 0.48 ml/minute. Once DMAPMA/water flow started, initiated with first shot of Vazo® 67 in IPA (Time 0).
7. Initiator was added at 0, 30, 60, 150 and 210 minutes. 0.44 g of Vazo 67 in 1.3 g IPA was added for each shot and two 0.7 g IPA washes were made.
8. Held the reaction temperature overnight at 70° C.
9. When residual VP was below 400 ppm, diluted the batch with 297.5 g Dl water. p0 10. Cooled batch to 50° C.
11. Neutralized the batch with 19.56 g diethyl sulfate (DES) over 60 minutes; at flow rate of 0.28 g/ml.
12. Stirred for 2 hours.
13. Product.

EXAMPLE 6

VP/DMAPMA/PETE Neutralized with Benzophenone-4

1. To a 2-l kettle fitted with a nitrogen inlet tube, thermocouple, agitator, and feed lines was added 87.15 g of HPVP, 630 g Dl water and 0.33 g PETE (0.30% based upon monomer).
2. Purged with nitrogen subsurface for 30 minutes.
3. Heated to 70° C.
4. Weighed out 22.69 g DMAPMA and 67 g Dl water. Purged with nitrogen.
5. When kettle temperature was at 70° C., stopped subsurface nitrogen purge and purged above surface. Precharged 4.23 g DMAPMA/water from container.
6. Started a continuous addition of the remaining DMAPMA/water (85.46 g) over 210 minutes. Flow rate 0.40 ml/minute. Once DMAPMA/water flow started, initiated with first shot of Vazo® 67 in IPA (Time 0).
7. Initiator was added at 0, 30, 60, 150 and 210 minutes. 0.4 g of Vazo 67 in 1.0 g IPA was added for each shot and two 0.5 g IPA washes were made.
8. Held the reaction temperature overnight at 70° C.
9. When residual VP was below 400 ppm, diluted the batch with 266.7 g Dl water.
10. Cooled batch to 50° C.
11. Neutralized the batch with benzophenone-4, 5 to 99 mole % (2 to 38.6 g respectively). Continued neutralization with sulfuric acid to pH of 6.8 to 7.8 at 50 C.
12. Cooled and discharged.
13. Product.

EXAMPLE 7

VP/DMAPMA/PETA

1. To a 2-l kettle fitted with a nitrogen inlet tube, thermocouple, agitator, and feed lines was added 104.58 g of HPVP, 756 g Dl water and 0.59 g pentaerythritol tetra acrylate (0.30% based upon monomer).
2. Purged with nitrogen subsurface for 30 minutes.
3. Heated to 70° C.
4. In a separate container, weighed out 27.23 g DMAPMA and 80.4 g Dl water. Purged with nitrogen.

5. When kettle temperature was at 70° C., stopped subsurface nitrogen purge and purged above surface. Precharged 5.38 g DMAPMA/water from container.
6. Started continuous addition of the remaining DMAPMA/water (102.25 g) over 210 minutes. Flow rate 0.52 ml/minute. Once DMAPMA/water flow started, initiated with first shot of Vazo®67 in IPA (Time 0).
7. Initiator was added at 0, 30, 60, 150 and 210 minutes. 0.16 g of Vazo® 67 in 1.0 g IPA was added for each shot and two 0.5 g IA washes were made.
8. Held the reaction temperature overnight at 70° C.
9. When VP was below 400 ppm, diluted the batch with 266.7 g Dl water.
10. Cooled batch to 50° C.
11. Neutralized the batch with conc. sulfuric acid to pH of 6.6 to 7.8 at 25° C.
12. Added 0.15 to 0.19% BTC 50 NF as preservative.
13. Product.

EXAMPLE 8

Crosslinked Vinyl Caprolactam/DMAPMA Copolymer

1. To a 2-l kettle fitted with a nitrogen inlet tube, thermocouple, agitator and feed lines was added 130.7 g vinyl caprolactam, 128.7 g Dl water, 171.6 g ethanol, and 0.88 g PETE (0.6% based upon monomer).
2. Purged with nitrogen for 30 minutes.
3. Heated to 70° C.
4. In a syringe pump was added 32.98 g DMAPMA and 171.6 g Dl water.
5. At 70° C. added 40 ml of the DMAPMA/water mixture to the kettle and added the first shot of initiator, 0.075 g Vazo® 67 in 0.75 g ethanol. Washed with 0.75 g ethanol.
6. Started addition of the remaining DMAPMA/water mixture (Time 0) from the syringe pump at a rate of 0.34 ml/min, added over 480 minutes.
7. At time 60, 120, 180, 240, 300, 360, 420 and 480 minutes added a shot of Vazo® 67, 0.075 g in 0.75 g ethanol. Washed with 0.75 g ethanol.
8. Held at 70° C. overnight.
9. Cooled reaction to 30° C. and added 415.6 g Dl water.
10. Mixed until uniform and then added 544.4 g Dl water and 15.38 g hydrochloric acid.
11. Mixed for 2 hours. Adjusted pH to 6.6 to 7.8 with hydrochloric acid, if necessary.
12. Added 0.15 to 0.19% BTC-50 NF as preservative.
13. Product.

EXAMPLE 9

VP/DMAEMA/PETE Process

1. To a 2-l kettle fitted with a nitrogen inlet tube, thermocouple, agitator, and feed lines is added 87.15 g of HPVP, 630 g Dl water and 0.33 g (0.30% based upon monomer) pentaerythritol triallyl ether.
2. Purged with nitrogen subsurface for 30 minutes.
3. Heated to 70° C.
4. In a separate container, weighed out 22.69 g DMAEMA and 67 g Dl water. Purged with nitrogen.
5. When kettle temperature was at 70° C., stopped subsurface nitrogen purge and purged above surface. Precharged 4.23 g DMAEMA/water from container.
6. Started continuous addition of the remaining DMAEMA/water (85.46 g) over 210 minutes. Flow rate 0.40 ml/minute. Once DMAEMA/water flow started initiator addition with first shot of Vazo 67 in IPA (Time 0).
7. Initiator was added at 0, 30, 60, 150, and 210 minutes. 0.4 g of Vazo 67 in 1.0 g IPA was added for each shot and two 0.5 g IPA washes were made.
8. Held the reaction temperature overnight at 70° C.
9. When VP was below 400 ppm, diluted the batch with 266.7 g Dl water.
10. Cooled batch to 50° C.
11. Neutralized the batch with conc. HCl to pH of 6.2 to 6.8 at 50° C. Room temperature pH will be 6.8 to 7.2. Required approximately 14 g of conc. HCl.
12. Added 0.15 to 0.19% BTC 50 NF as preservative.

EXAMPLE 10

Drying of Example 9

The solution of Example 9 was dried on a drum dryer to a solids of >95%. The Tg of the powder was 167° C. Then it was reconstituted in water and found to provide the same waterproofing as the original solution.

EXAMPLE 11

Particle Isolation and Properties 95.2 g of approximately 10% solids polyvinylpyrrolidone/PETE was diluted in 2-liters of distilled water and stirred until thoroughly mixed. A second solution was prepared by taking 500 ml of the first solution and diluting in 2-liters of distilled water. Stirred until thoroughly mixed. Poured the second solution into four 16 oz. jars and centrifuged at ~2250 rpm for about 90 minutes. A white precipitate was observed on the bottom of each 16 oz. jar. The precipitate was removed, via pipette, and placed into four 8-dram vials, respectively. The four 8-dram vials were centrifuged at ~3000 rpm for 60 minutes. The particle size on the precipitate was measured using a Microtrak UPA and found to be about 4 nm.

EXAMPLE 11A

The precipitate obtained in Example 11 in three 8-dram vials was dried, in vacuo, in a 40° C. oven overnight. The result was a thin, generally clear film upon visual observation. This material was then exposed to either methanol, diethyl ether and n-heptane. After 24 hours, methanol had re-dispersed the material. Diethyl ether and n-heptane did not appear to effect the dried material. After 14 days, all samples exhibited a similar appearance to the original 24 hour observations. The particle size on the methanol dispersed material was measured using a Microtrak UPA and found to be about 4 μm.

COMPARATIVE EXAMPLE 12

An aqueous solution of 119.64 g of vinyl pyrrolidone monomer, 0.36 g pentaerythritol trially ether (PETE), 0.6 g of Vazo 67, and 480 g water was charged to a kettle and purged with nitrogen. The reaction mixture was then heated to 65° C. while stirring at 650 rpm. Within 25 minutes the product became so viscous that the reaction was stopped. The product was a continuous gel only.

COMPARATIVE EXAMPLE 13

An aqueous solution of 119.64 g of vinyl pyrrolidone monomer, 0.36 g pentaerythritol triallyl ether (PETE), 0.23 g of Vazo 67, and 480 g water was charged to a kettle and purged with nitrogen. The reaction mixture was then heated to 65° C. while stirring at 650 rpm. After 2 hours at 65° C., the reaction was heated to 95° C. for 1 hour. The product was a viscous solution only.

EXAMPLE 14

DPI Film Coating Formulation

| Ingredient | Parts by Weight |
|---|---|
| VP/DMAPMA/PETE (Ex. 1) | 2.00 |
| PV-OH (88% hydrolyzed) | 8.00 |
| Sequrez ® 755 (glyoxyl) | 0.75 |
| Water | 89.25 |
| | 100.00 |

EXAMPLE 15

UV Coating Formulation

| Ingredient | Parts by Weight |
|---|---|
| VP/DMAPMA/PETE/BENZO-4 (Ex. 6) | 2.00 |
| PV-OH (88% hydrolyzed) | 8.00 |
| Sequrez ® 755 (glyoxyl) | 0.75 |
| Water | 89.25 |
| | 100.00 |

EXAMPLE 16

SUNSCREEN CREAM

| Ingredients | Wt. % |
|---|---|
| PHASE A | |
| Deionized water | 15.69 |
| Disodium EDTA | 0.10 |
| Acrylates/Steareth-20 Methacrylate Copolymer | 1.00 |
| Acrylates Copolymer | 1.00 |
| Hexylene Glycol | 1.00 |
| Glyceryl Polymethacrylate and Propylene Glycol and PVM/MA Copolymer | 0.50 |
| VP/DMAPMA/PETE/Benzophenone-4 Copolymer (Ex. 6) | 50.00 |
| PHASE B | |
| Glyceryl Stearate and Behenyl Alcohol and Palmitic and Stearic Acid and Lecithin and Lauryl and Myristyl Alcohol and Cetyl Alcohol | 5.00 |
| Oxybenzone | 3.00 |
| Octyl Salicylate | 3.00 |
| Tridecyl Neopentanoate | 2.00 |
| Octyl Palmitate | 6.00 |
| Myristyl Myristate | 1.00 |
| PHASE C | |
| Deionized Water | 5.00 |
| NaOH, 10% Solution | 1.26 |

SUNSCREEN CREAM -continued

| Ingredients | Wt. % |
|---|---|
| PHASE D | |
| Diazolidinyl Urea and Iodopropynyl Butylcarbamate | 0.50 |
| Methyl Paraben | 0.20 |
| Hexylene Glycol | 1.00 |
| PHASE E | |
| Fragrance | 0.25 |

Procedure
1. Combine ingredients in Phase A and heat to 70–75° C.
2. Combine ingredients in Phase B and mix and heat to 70–75° C.
3. Add Phase B to Phase A under homogenization.
4. Add Phase C to the batch under homogenization and homogenize for 15 minutes.
5. Switch to propeller mixing and cool to 45° C.
6. Add Phase D at 45° C. Add Phase E at 40° C. QS with water.

The UV absorbance of the cream was enhanced by the presence of the polymeric composition of the invention therein, as compared to similar formulations without this composition, generally an increase of about 2–3 SPF numbers.

EXAMPLE 17

Clear Styling/Conditioning Gel

| Ingredients | Wt. % |
|---|---|
| Deionized Water | 74.60 |
| Ethanol (190 Proof) | 5.00 |
| VP/DMAPMA/PETE Copolymer (Ex. 1) | 20.00 |
| Dimethicone Copolyol | 0.10 |
| Caprylyl Pyrrolidone | 0.10 |
| Panthenol | 0.10 |
| 2,4-Dihydroxy-N-(3-hydroxypropyl)-3,3-Dimethyl Butanamide | |
| Diazolidinyl Urea and Iodopropynyl Butylcarbamate | 0.10 |
| Perfume | qs |

Manufacturing Procedure
1. In a vessel, add ethanol to water and stir until homogeneous.
2. Next, add VP/DMAPMA/PETE copolymer to the mixture and stir well until homogeneous.
3. Add dimethicone copolyol, panthenol and caprylyl pyrrolidone to the mixture and stir well after each addition until homogeneous.
4. Next, add diazolidinyl urea and iodopropynyl and butylcarbamate and stir well until homogeneous.

EXAMPLE 18

Rinse-Off Protection Hair Conditioner

| Ingredients | Wt. % |
|---|---|
| Deionized Water | 81.73 |
| Emulsifying Wax NF | 4.00 |

-continued

Rinse-Off Protection Hair Conditioner

| Ingredients | Wt. % |
|---|---|
| Cetearyl Alcohol and Ceteareth-20 | 2.00 |
| Propylene Glycol | 1.00 |
| VP/DMAPMA/PETE Neutralized with Benzophenone-4 (Ex. 6) | 10.00 |
| Glycerin 99.7% | 0.50 |
| Lauryl Pyrrolidone | 0.25 |
| Citric Acid FCC, USP, Anhydrous | 0.02 |
| Propylene Glycol and Diazolidinyl Urea and Iodopropynyl butylcarbamate | 0.50 |

Manufacturing Procedure
1. Heat the water, propylene glycol, glycerin, and citric acid to 80–85° C. using continuous addition with a propeller stir rod.
2. Add the VP/DMAPMA/PETE neutralized with Benzophenone-4 and stir to homogeneous.
3. Combine in a separate vessel lauryl pyrrolidone, emulsifying wax NF, cetearyl alcohol and ceteareth-20, heating to 80–85° C. mixing until homogeneous.
4. Add, product step 3, to the water phase with good agitation. Mix with continuous agitation for 10–20 minutes or longer. Maintain temperature at 80–85° C. during this step.
5. Begin cooling with continuous agitation until approximately 45° C. Do not force cool.
6. Switch to a paddle mixing rod. Continue slow agitation and cool until a temperature of 30–35° C. is reached. At 30–35° C. add the propylene glycol and diazolidinyl urea and iodopropynyl butylcarbamate and continue mixing until 25° C. is reached.

EXAMPLE 19

Polymeric Coatings on a Substrate

Films were cast of 0.5 mil thickness on a 3.25×4×⅟₁₆ inch glass plate from 11% by weight aqueous polymeric solutions prepared (a) with no particles and (b) with the particle-containing polymeric solutions of Example 1 (51% particles). The resulting films which contained no UV protectant additives and had a coating volume of about 1.3 $\mu L/cm^2$. The UV (and SPF) spectroscopic results via a Solar Protection Measurement System indicated that the presence of polymeric particles in the film coating increased its ability to absorb UV radiation, and showed an increase in the SPF number from 2.3 to 5.3. The coating also was non-irritating, non-toxic, water-resistant and visually clear.

EXAMPLE 20

Pharmaceutical Tablet Composition

| Acetaminophen | 93.5% |
|---|---|
| PVP/PETE (in place of Polyplasdone K-90) | 4% |
| Polyplasdone XL | 2% |
| Magnesium Stearate | 0.5% |
| Total | 100% |

EXAMPLE 21

Refractive Index Modification

VP/DMAPMA/PETE copolymer was neutralized with 4-benzophenone (Escalol® 557). The refractive index of the film was measured using a Model 2010 Prism Coupler on the bulk material by pressing the film against a prism. The result of this test demonstrates the ability to modify the refractive index of these polymeric film compositions by strategically selecting the neutralization acid.

| Sample | Refractive Index |
|---|---|
| VP/DMAPMA/Sulfuric Acid | 1.52 |
| VP/DMAPMA/PETE/HCl | 1.52 |
| VP/DMAPMA/PETE/4-Benzophenone | 1.55 |

EXAMPLE 22

Commercial Uses for the Invention Aqueous Polymers Containing In Situ-formed Polymeric Particles 1. UV protectants (coatings)
2. Sunscreen
3. Drug delivery systems (smart-delivery, smart-release)
4. Transdermal drug systems
5. Sizing (fabric coating)
6. Dye transfer inhibition
7. Autowaxes
8. Agricultural coatings/delivery
9. Personal care (hair care applications)
10. Abrasives (industrial and personal)
11. Encapsulates systems (entrapments)
12. Dispersants
13. Electro/optical systems

What is claimed is:

1. A stable, aqueous polymeric composition which forms a clear to translucent film upon application to a substrate consisting essentially of, (a) a water-soluble, or copolymer thereof with a water soluble monomer, having (b) in situ-formed, substantially water-insoluble, crosslinked resinous particles of said polymer or copolymer substantially uniformly dispersed in the composition, and (c) water.

2. A composition according to claim 1 wherein said polymer is polyvinylpyrrolidone (PVP) or polyvinylcaprolactam (PVCL).

3. A composition according to claim 1 comprising, by weight, 5–75% of (a) and (b), and 25–95% of water.

4. A composition according to claim 1 wherein said polymer is a copolymer of PVP or PVCL, and one or more comonomers.

5. A composition according to claim 4 wherein said comonomer is dimethylaminopropyl(meth)acrylamide (DMAPMA) and/or dimethylaminoethyl(meth)acrylate (DMAEMA).

6. A composition according to claim 1 wherein said polymer is a copolymer of PVP and PVCL, and, optionally, one or more comonomers.

7. A composition according to claim 1 wherein said particles are <500$\mu$.

8. A composition according to claim 7 wherein said particles are <100$\mu$.

9. A composition according to claim 8 wherein said particles are >1 nm and >100 $\mu$.

10. A composition according to claim 1 wherein said polymer is neutralized and/or functionally neutralized and/or quaternized, and/or functionalized quaternized.

11. A composition according to claim 1 wherein the ratio of (a):(b) is 20–95% to 5–80%.

12. A composition according to claim 11 wherein said ratio is 20–75% to 25–80%.

13. A composition according to claim 1 wherein said crosslinking agent is a substantially water-insoluble compound.

14. A composition according to claim 13 wherein said crosslinking agent is pentaerythritol triallyl ether (PETE), or pentaerythritol tetraacrylate (PETA).

15. A composition according to claim 10 wherein said functional neutralization acid is a UV active based upon derivatives of cinnamic and/or benzoic and/or sulfonic and/or acetic and/or terephthalic and/or maleic acids.

16. A composition according to claim 10 wherein said functional neutralization acid is a pharmaceutically active acid.

17. A composition according to claim 10 wherein said functional neutralization acid contains silicone.

18. A composition according to claim 10 wherein said functional neutralization acid modifies the refractive index of the polymer film composition.

19. A composition according to claim 14 wherein said crosslinking agent is present in an amount of 0.02–0.5% by weight of said composition.

20. A composition of claim 19 wherein said amount is 0.05–0.3%.

21. A composition of claim 1 having a Brookfield viscosity of 1,000 to 45,000 cps.

22. A composition of claim 21 wherein said viscosity is 2,000 to 20,000.

23. A composition of claim 1 wherein said polymer is a vinyl lactam polymer, optionally copolymerized with a methacrylate/acrylate and/or methacrylamide/acrylamide comonomer.

24. A process for making the stable, aqueous polymeric composition of claim 1 which comprises providing a reaction mixture of a water-soluble monomer, optionally with one or more water-soluble comonomers, a predetermined amount of a crosslinking agent and water, heating the mixture, then periodically adding a predetermined amount of an initiator, and polymerizing at about 30–130° C.

25. A process according to claim 24 further including the step of diluting with water and/or alcohol during or after the polymerization.

26. A process according to claim 24 in which said crosslinking agent is present in an amount of 0.02–0.5 wt. % based on monomers present.

27. A process according to claim 24 wherein said crosslinker is pentaerithritol triallyl ether or pentaerithritol tetraacrylate.

28. A process according to claim 24 wherein said initiator is an azo initiator.

29. A process according to claim 24 wherein said water soluble monomer is a vinyl monomer.

30. A formulation containing the composition of claim 1.

31. A film of the composition of claim 1 on a substrate.

32. A composition according to claim 1 wheren said crosslinker is at least partially insoluble in water.

33. A composition according to claim 1 which is dried to provide the polymeric composition as a solid.

34. A composition according to claim 33 wherein the water soluble polymer is extracted with a solvent.

35. A dry, stable polymeric composition consisting essentially of, (a) a water-soluble polymer, or copolymer with a water soluble, and (b) in situ-formed, substantially water-insoluble resinous particles of said polymer or copolymer which is a crosslinked polymer or copolymer substantially uniformly dispersed in said composition.

36. A composition which comprises substantially water-insoluble resinous particles of an in situ-formed polymer which is a crosslinked polymer.

37. A dry stable polymeric composition of claim 35 comprising, by weight, (a) 20 to 95% and (b) 5 to 80%.

38. A composition of claim 35 wherein said particles are >1 nm and <500μ.

39. A formulation which includes the dry polymeric composition of claim 35.

* * * * *